(12) United States Patent
Ferguson

(10) Patent No.: US 6,592,622 B1
(45) Date of Patent: Jul. 15, 2003

(54) APPARATUS AND METHOD FOR SECURING SOFT TISSUE TO AN ARTIFICIAL PROSTHESIS

(75) Inventor: Joe W. Ferguson, Warsaw, IN (US)

(73) Assignee: DePuy Orthopaedics, Inc., Warsaw, IN (US)

(*) Notice: Subject to any disclaimer, the term of this patent is extended or adjusted under 35 U.S.C. 154(b) by 122 days.

(21) Appl. No.: 09/695,464

(22) Filed: Oct. 24, 2000

(51) Int. Cl.$^7$ ................................................ A61F 2/08
(52) U.S. Cl. .................. 623/13.14; 623/13.18; 623/16.11; 623/20.17; 623/13.12; 623/23.75
(58) Field of Search ................ 623/13.12, 13.14, 623/13.11, 13.18, 13.17, 13.19, 13.2, 11.11, 16.11, 20.17, 20.28, 20.32, 23.75, 23.76

(56) References Cited

U.S. PATENT DOCUMENTS

| | | | |
|---|---|---|---|
| 3,176,316 A | * | 4/1965 | Bodell ..................... 623/13.19 |
| 3,545,008 A | * | 12/1970 | Bader ...................... 623/13.15 |
| 3,896,500 A | | 7/1975 | Rambert et al. |
| 3,988,783 A | | 11/1976 | Treace |
| 4,149,277 A | | 4/1979 | Bokros |
| 4,246,660 A | | 1/1981 | Wevers |
| 4,411,027 A | | 10/1983 | Alexander et al. |
| 4,585,458 A | | 4/1986 | Kurland |
| 4,894,063 A | * | 1/1990 | Nashef ..................... 623/13.17 |
| 5,116,373 A | | 5/1992 | Jakob et al. |
| 5,376,119 A | | 12/1994 | Zimmermann et al. |
| 5,393,302 A | | 2/1995 | Clark et al. |
| 5,425,767 A | | 6/1995 | Steininger et al. |
| 5,445,833 A | | 8/1995 | Badylak et al. |
| 5,769,894 A | | 6/1998 | Ferragamo |
| 5,782,915 A | | 7/1998 | Stone |
| 5,899,938 A | | 5/1999 | Sklar et al. |
| 6,045,574 A | | 4/2000 | Thal |
| 6,080,192 A | * | 6/2000 | Demopulos et al. ..... 623/13.14 |

* cited by examiner

Primary Examiner—Paul B. Prebilic
(74) Attorney, Agent, or Firm—Maginot Moore & Bowman

(57) ABSTRACT

An apparatus for securing soft tissue to a prosthesis includes a retaining member secured to the prosthesis. The apparatus also includes a first band constructed of a resorbable material. The first band has a first end portion, a middle portion, and a second end portion. The apparatus also includes a second band constructed of a biologically inert material. The second band has a first end portion, a middle portion, and a second end portion. The middle portion of the first band is positioned around a retaining portion of the retaining member such that both the first end portion and the second end portion of the first band extend outwardly from the retaining member. The middle portion of the second band is positioned around the retaining portion of the retaining member such that both the first end portion and the second end portion of the second band extend outwardly from the retaining member. Each of the first end portion of the first band, the second end portion of the first band, the first end portion of the second band, and the second end portion of the second band is adapted to be secured to the soft tissue.

24 Claims, 4 Drawing Sheets

US 6,592,622 B1

APPARATUS AND METHOD FOR SECURING SOFT TISSUE TO AN ARTIFICIAL PROSTHESIS

TECHNICAL FIELD OF THE INVENTION

The present invention relates generally to a prosthesis, and more particularly to an apparatus and method for securing soft tissue to an artificial prosthesis.

BACKGROUND OF THE INVENTION

During the lifetime of a patient, it may be necessary to perform a joint replacement procedure on the patient as a result of, for example, disease or trauma. Such a joint replacement procedure may involve the use of a prosthetic component or prosthesis to replace a portion of the patient's natural bone. Heretofore designed prosthesis are generally constructed of a metallic or composite material. A problem arises when such metal or composite prosthesis are utilized to replace a relatively large portion of a bone. In particular, if a large portion of a patient's natural bone must be replaced with a prosthesis, it is generally difficult to attach the soft tissue required for joint operation (e.g. ligaments and tendons) to the implanted prosthesis. For example, as a result of cancer or other type of disease, the entire proximal end portion of a patient's tibia may have to be removed and replaced with a tibial prosthesis. In such a case, the natural point of connection for the distal end portion of the patient's patellar ligament (i.e. the tibial tuberosity) is also removed. Hence, the distal end portion of the patient's patellar ligament must then be secured to the tibial prosthesis in order to provide for functional operation of the patient's knee.

A number of approaches have heretofore been taken in an attempt to attach soft tissue such as ligaments and tendons to a metal or composite prosthesis. The most common approach has been to configure the prosthesis with a number of suture holes to which the soft tissue (e.g. a ligament or tendon) may be sutured. One problem with this approach is that the soft tissue has no source of nourishment. Moreover, such a configuration of the prosthesis does not provide adequate surface features or the like for facilitating ingrowth or anchoring of the soft tissue to the prosthesis.

Another approach which has been utilized involves the use of an allograft or composite allograft prosthesis in lieu of a metal or composite prosthesis. Such prosthesis are generally harvested from a donor upon death thereof and then frozen until needed. However, the availability of allograft prostheses is becoming more and more scarce. Moreover, even when available, such harvested allograft prostheses often times do not possess the requisite number of tissue attachment sites. In addition, patients requiring the joint replacement procedure are sometimes either very large or very small in size which can make the procurement of a properly sized allograft prosthesis very difficult.

Yet another approach which has been utilized involves the use of bone plugs and grafts which are threaded into or otherwise secured to the prosthesis. However, this approach suffers from many of the same drawbacks as does the use of an allograft prosthesis. Moreover, since bone plugs are constructed of dead tissue, they tend to become brittle over time and eventually break down under heavy loads.

What is needed therefore is an apparatus and method for securing soft tissue to a prosthesis which overcomes one or more of the above-mentioned drawbacks. What is particularly needed is an apparatus and method for securing soft tissue to a prosthesis which provides enhanced mechanical anchoring of the soft tissue while also stimulating or otherwise facilitating tissue ingrowth.

SUMMARY OF THE INVENTION

In accordance with one embodiment of the present invention, there is provided an apparatus for securing soft tissue to a prosthesis. The apparatus includes a retaining member secured to the prosthesis. The apparatus also includes a first band constructed of a resorbable material. The first band has a first end portion, a middle portion, and a second end portion. The apparatus also includes a second band constructed of a biologically inert material. The second band has a first end portion, a middle portion, and a second end portion. The middle portion of the first band is positioned around a retaining portion of the retaining member such that both the first end portion and the second end portion of the first band extend outwardly from the retaining member. The middle portion of the second band is positioned around the retaining portion of the retaining member such that both the first end portion and the second end portion of the second band extend outwardly from the retaining member. Each of the first end portion of the first band, the second end portion of the first band, the first end portion of the second band, and the second end portion of the second band is adapted to be secured to the soft tissue.

In accordance with another embodiment of the present invention, there is provided an apparatus for securing soft tissue to a prosthesis. The apparatus includes a retaining member secured to the prosthesis. The retaining member has a retaining surface. The apparatus also includes an inner band having a first end portion, a middle portion, and a second end portion. The apparatus further includes an outer band having a first end portion, a middle portion, and a second end portion. The middle portion of the inner band is positioned in contact with the retaining surface of the retaining member such that both the first end portion and the second end portion of the inner band extend outwardly from the retaining member. The outer band is secured to the inner band such that (a) the first end portion of the outer band is positioned in contact with the first end portion of the inner band, (b) the middle portion of the outer band is positioned in contact with the middle portion of the inner band, and (c) the second end portion of the, outer band is positioned in contact with the second end portion of the inner band. Each of the first end portion of the inner band, the second end portion of the inner band, the first end portion of the outer band, and the second end portion of the outer band is adapted to be secured to the soft tissue.

In accordance with a further embodiment of the present invention, there is provided a method of securing soft tissue to a prosthesis. The prosthesis has a retaining member secured thereto. The method includes the step of looping a first end portion of a first band around the retaining member such that both the first end portion of the first band and a second end portion of the first band extend outwardly from the retaining member. The method also includes the step of looping a first end portion of a second band around the retaining member such that both the first end portion of the second band and a second end portion of the second band extend outwardly from the retaining member. In addition, the method includes the step of securing the soft tissue to (i) the first end portion and the second end portion of the first band, and (ii) the first end portion and the second end portion of the second band.

In accordance with yet another embodiment of the present invention, there is provided a prosthesis assembly. The prosthesis assembly includes a prosthetic component having a retaining member secured thereto. The prosthesis assembly also includes a first band constructed of a resorbable material. The first band is adapted to be secured to both the retaining member and the soft tissue. The prosthesis assembly also includes a second band constructed of a biologically inert material. The second band is adapted to be secured to both the retaining member and the soft tissue.

It is therefore an object of the present invention to provide a new and useful apparatus for securing soft tissue to a prosthesis.

It is moreover an object of the present invention to provide an improved apparatus for securing soft tissue to a prosthesis.

It is a further object of the present invention to provide a new and useful method of securing soft tissue to a prosthesis.

It is also an object of the present invention to provide an improved method of securing soft tissue to a prosthesis.

It is yet another object of the present invention to provide an apparatus and method for securing soft tissue to a prosthesis which provides enhanced mechanical anchoring of the soft tissue while also stimulating or otherwise facilitating tissue ingrowth.

The above and other objects, features, and advantages of the present invention will become apparent from the following description and the attached drawings.

DETAILED DESCRIPTION OF THE INVENTION

Figure 1:
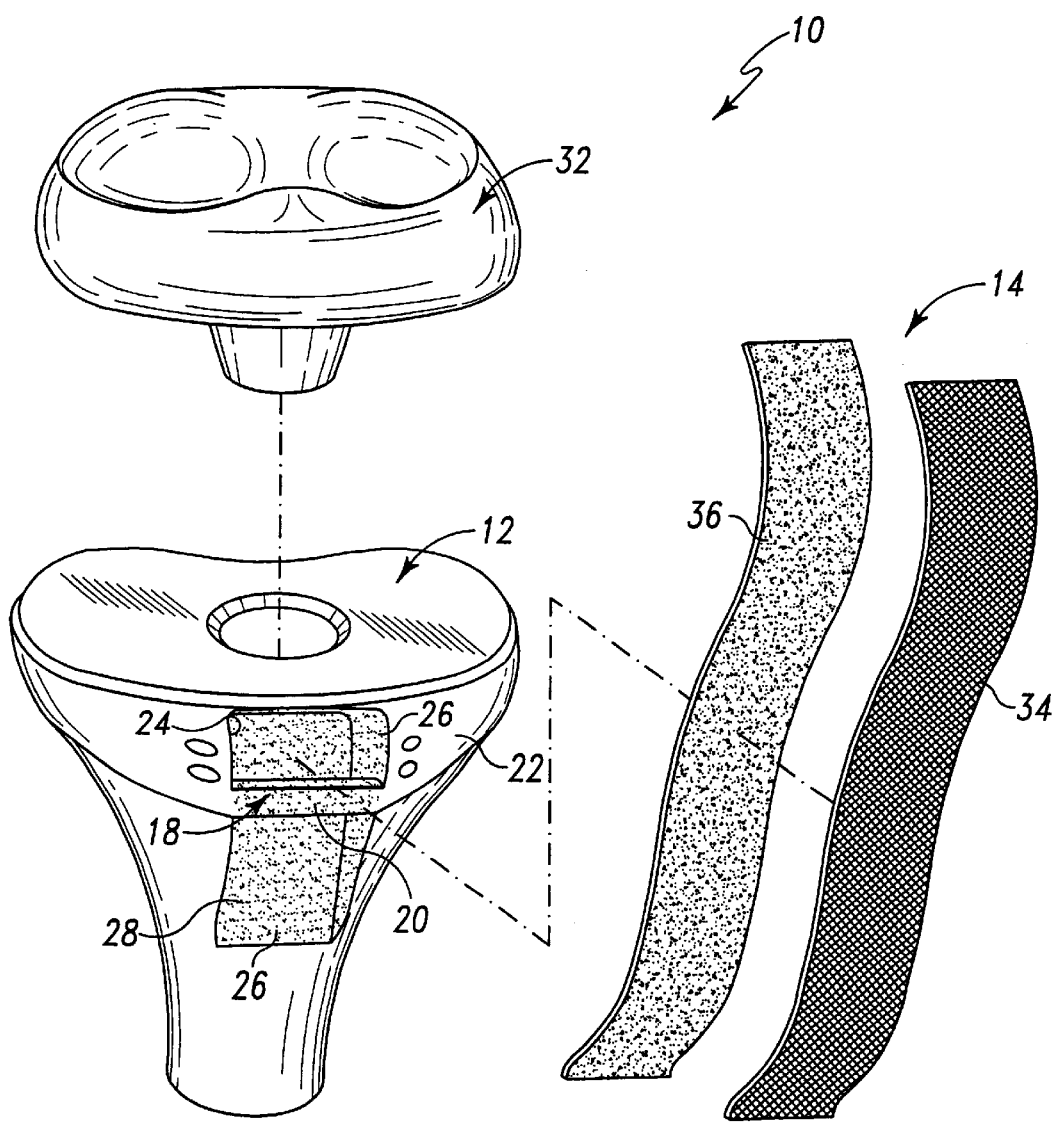
FIG. 1 is a perspective view of a prosthesis assembly which incorporates the features of the present invention therein.

While the invention is susceptible to various modifications and alternative forms, specific embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Figure 2:
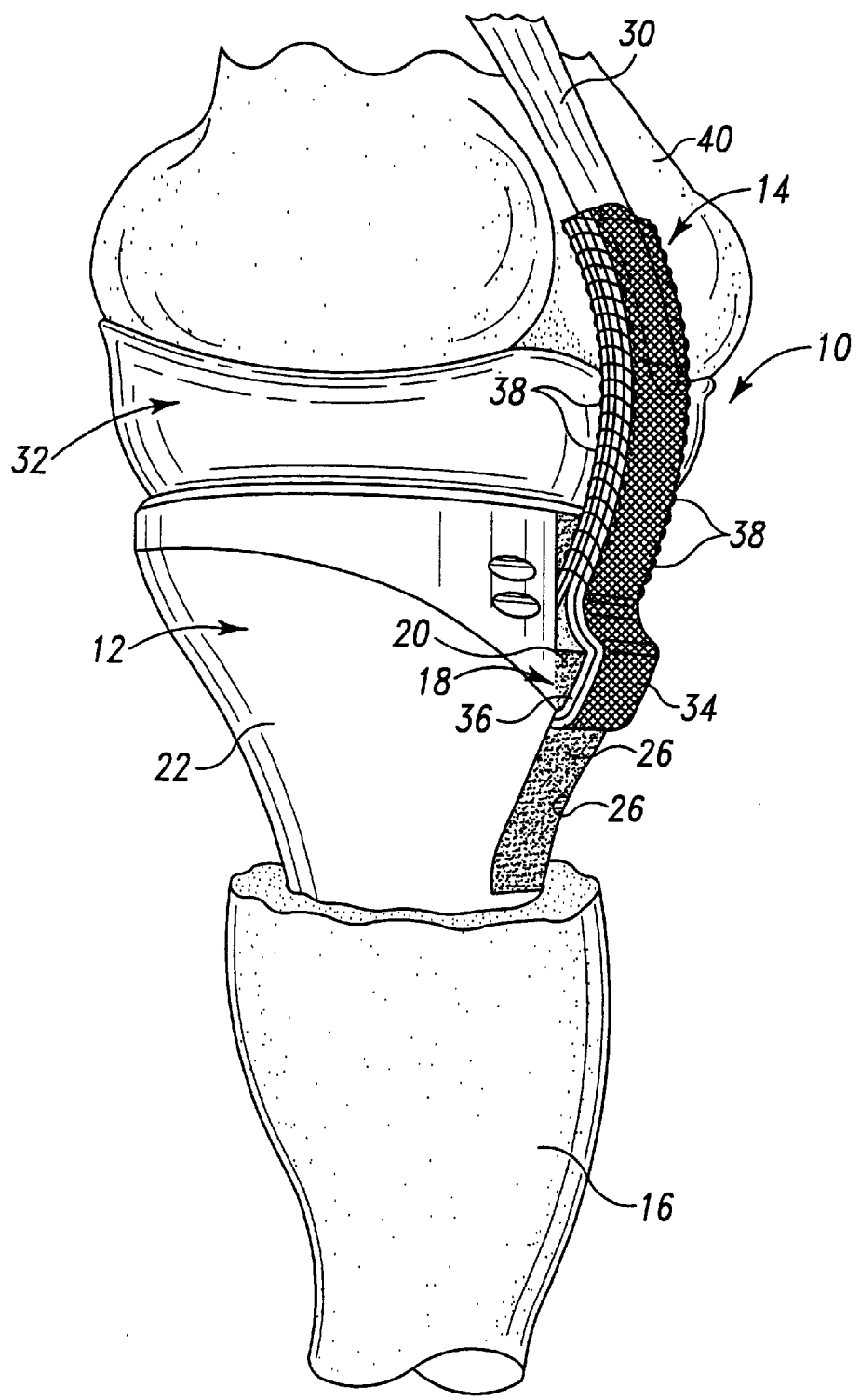
FIG. 2 is a fragmentary perspective view which shows the prosthesis assembly of FIG. 1 secured to a patient's femur.

Referring now to FIGS. 1-2, there is shown a prosthesis assembly 10 for use during performance of a joint replacement procedure such as a knee replacement procedure. The prosthesis assembly 10 includes a prosthetic component such as a tibial prosthesis 12 and a band assembly 14. The tibial prosthesis 12 is configured to be implanted into a tibia 16 of a patient. It should be appreciated that the tibial prosthesis 12 may be adapted to replace any portion of the patient's tibia 16. In the exemplary embodiment described herein, the tibial prosthesis 12 is adapted to replace substantially all of the proximal end of the patient's tibia 16 including the tibial tuberosity (not shown) to which the distal end portion of the patient's patellar ligament 30 (or loosely, the patella tendon) is attached.

It should be appreciated that although the present invention is herein described in regard to attachment of the patellar ligament 30 to the tibial prosthesis 12, the concepts of the present invention may be utilized to secure numerous other types of soft tissue (e.g. ligaments and tendons) at numerous joint locations throughout the body. For example, the concepts of the present invention may be utilized to attach other ligaments and tendons within the knee, or may also be utilized to attach ligaments and tendons associated with the hip or shoulder joints to a hip or shoulder prosthetic component, respectively.

The tibial prosthesis 12 is constructed of a material that is biologically suitable for implantation into the patient's body. Typically, the tibial prosthesis 12 is constructed of a metal such as biological grade stainless steel or titanium. The tibial prosthesis 12 may also be constructed of other types of materials such as composite materials. It should be appreciated that the concepts of the present invention are useful for attaching soft tissue to the tibial prosthesis 12 irrespective of the type of material utilized in the construction of the tibial prosthesis 12.

The tibial prosthesis 12 has a retaining member 18 secured thereto. As shall be discussed below in greater detail, the retaining member 18 is utilized to secure the band assembly 14 to the tibial prosthesis 12. The retaining member 18 may be embodied as any type of retaining structure to which the band assembly 14 may be secured. For example, the retaining member 18 may be embodied as a protrusion, hook, clamping mechanism, or similar type of structure. In the exemplary embodiment shown in FIGS. 1 and 2, the retaining member 18 is configured as a retaining bar 20. As shown in FIG. 1, the retaining bar 20 is integrally formed with a body 22 of the tibial prosthesis 12; however, the retaining bar 20 could alternatively be a separate component which is removably secured to the body 22 by use of removable fasteners such as bolts or screws (not shown).

The body 22 of the tibial prosthesis 12 has a channel 24 defined therein. As shown in FIG. 1, the channel 24 is defined by the area between a number of sidewalls 26 which are machined or otherwise formed in the body 22 of the tibial prosthesis 12. Each end of the retaining bar 20 is secured to the body 22 proximate to the opposite sides of the channel 24. Such a configuration allows the retaining bar 20 to extend across the entire width of the channel 24. Moreover, the outer surface of the retaining bar 20 along with the outer surface of some or all of the sidewalls 26 has a porous material 28 disposed thereon. The porous material 28 is of the type which is commonly utilized in various orthopedic components to enhance bone tissue ingrowth into the component. However, in regard to the present invention, the use of the porous material 28 in the construction of the prosthesis assembly 10 facilitates long-term attachment of soft tissue to the prosthesis assembly 10. In particular, as discussed below in greater detail, the use of the porous material 28 in the construction of the tibial prosthesis 10 and the retaining member 18 of the present invention facilitates long-term attachment of the patellar ligament 30 to the tibial prosthesis 12.

The prosthesis assembly 10 also includes a bearing insert 32. The bearing insert 32 is provided to replace the patient's medial and/or lateral meniscus (not shown) thereby providing a bearing surface on which the lateral and medial condyles of the distal end of the patient's femur 40 may bear. The bearing insert 32 is preferably constructed from a polymeric material such as polyethylene or ultra-high molecular weight polypropylene (UHMWPE) thereby providing a desirable artificial surface on which the distal end of the patient's femur 40 may bear.

As shown in FIG. 1, the band assembly 14 includes an outer band 34 and an inner band 36. The outer band 34 provides mechanical strength along with a support structure for attaching the patellar ligament 30 to the tibial prosthesis 12. In essence, the outer band 34 functions as a "lattice" through which the patellar ligament 30 may grow in a direction toward the tibial prosthesis 12. As such, the outer band 34 may be constructed as a mesh type tape or a thin pliable band. The outer surfaces of the band 34 may be configured to include a porous material or other type of surface texture to facilitate the growth of the patellar ligament 30 along the length thereof. The outer band 34 is preferably constructed of a biologically inert material which possesses desirable mechanical properties such as a relatively high tensile strength and low fatigue characteristics. Examples of such a biologically inert material which may be utilized in the construction of the outer band 34 includes cobalt-chrome strips, marcylene tape, or Dacron tape.

The inner band 36, on the other hand, is provided to facilitate ingrowth of the patellar ligament 30 to the tibial prosthesis 30. As such, the inner band 36 is constructed of a resorbable material. What is meant herein by the term "resorbable material" is any material that stimulates or otherwise facilitates growth of natural soft tissue that gradually dissolves or is otherwise absorbed into the patient's body over time. Resorbable material may be a natural material, a synthetic material, or any combination of natural and synthetic materials. For example, the resorbable material of the present invention may take the form of a xenograft material such as small-intestinal submucosa (hereinafter "SIS"). Moreover, the resorbable material of the present invention may also take the form of synthetic materials such as Poly-(dioxanone) (hereinafter "PDS"), Poly-(glycolic acid) (hereinafter "PGA"), and Poly-(L-lactic acid) (hereinafter "PLLA").

It should also be appreciated that the bands 34, 36 of the band assembly 14 may be arranged in any desirable order. For example, although the band 34 is shown and described herein as being the "outer band", it should be appreciated that the position of the two bands 34, 36 may be swapped such that the band constructed of the resorbable material (i.e. the band 36) is positioned on the outside of the band constructed of the biologically inert material (i.e. the band 34).

As shown in FIG. 2, the band assembly 14 is looped around the retaining bar 20 and thereafter secured to the patellar ligament 30. In particular, a first end of the bands 34, 36 is advanced around the retaining bar 20 such that both ends of the bands 34, 36 extend outwardly from the retaining bar 20. When looped around the retaining bar 20 in such a manner, a middle portion of each of the bands 34, 36 is positioned around a retaining portion of the retaining bar 20 so as to retain the bands 34, 36. The term "retaining portion", as utilized in regard to the retaining member 18, refers to the portion of the retaining member 18 which is engaged (either directly or indirectly) by the band assembly 14. For example, in regard to the retaining bar 20, the upper surface, the back surface, and the lower surface of the retaining bar define retaining portions of the retaining bar 20.

As shown in FIG. 2, once the band assembly 14 has been looped around the retaining bar 20, the patellar ligament 30 is then secured thereto. In particular, the patellar ligament 30 is sandwiched or otherwise interposed between the respective end portions of the bands 34, 36. In such a configuration the patellar ligament 30 is interposed between the end portions of the inner band 36 which are, in turn, interposed between the end portions of the outer band 34. Thereafter, the patellar ligament 30 is sutured to the bands 34, 36 by use of a number of sutures 38 thereby securing the patellar ligament 30 to the band assembly 14 and hence the tibial prosthesis 12.

It should be appreciated from the above description that the bands 34, 36 of the band assembly 14 cooperate to provide both short-term and long-term attachment of the patellar ligament 30 to the tibial prosthesis 12. In particular, during the time period initially following the joint replacement procedure, the outer band 34 provides the mechanical strength (e.g. the tensile strength) necessary to maintain attachment of the patellar ligament 30 to the tibial prosthesis 12. During such an initial time period, the resorbable material associated with the inner band 36 (e.g. SIS) stimulates or otherwise facilitates growth of the patellar ligament 30 in a direction toward the tibial prosthesis 12. As described above, during such growth of the patellar ligament 30, the outer band 34 functions as a "lattice" for facilitating growth the growing patellar ligament 30 in a direction toward the tibial prosthesis 12.

Over time, the resorbable material of the inner band 36 is absorbed by the patient's body during continued growth of the patellar ligament 30. During such absorption of the inner band 36, the outer band 34 continues to provide the mechanical strength necessary to keep the growing patellar ligament 30 attached to the tibial prosthesis 12 thereby making up for any mechanical loss created by the dissolving inner band 36. Eventually, the patellar ligament 30 grows to a point in which it begins to ingrow into the porous material 28 disposed on the outer surface of the retaining bar 20 and the outer surface of the sidewalls 26 of the body 22 of the tibial prosthesis 12. Such ingrowth of the patellar ligament 30 into the porous material 28 of the retaining bar 20 and sidewalls 26 enables long-term attachment of the patellar ligament 30 to the tibial prosthesis 12.

Figure 3:
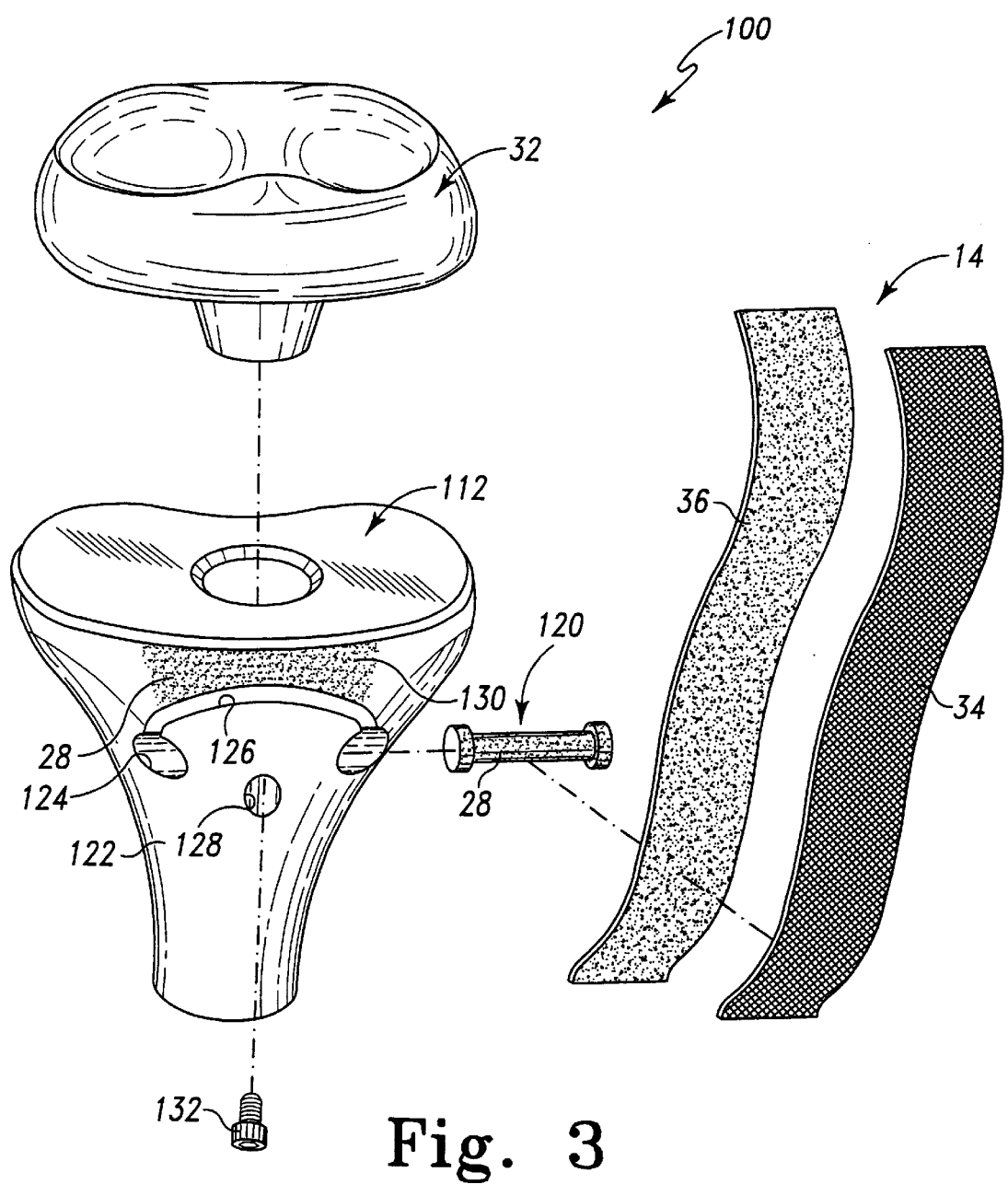
FIG. 3 is a view similar to FIG. 1, but showing a second embodiment of a prosthesis assembly which incorporates the features of the present invention therein.
Figure 4:
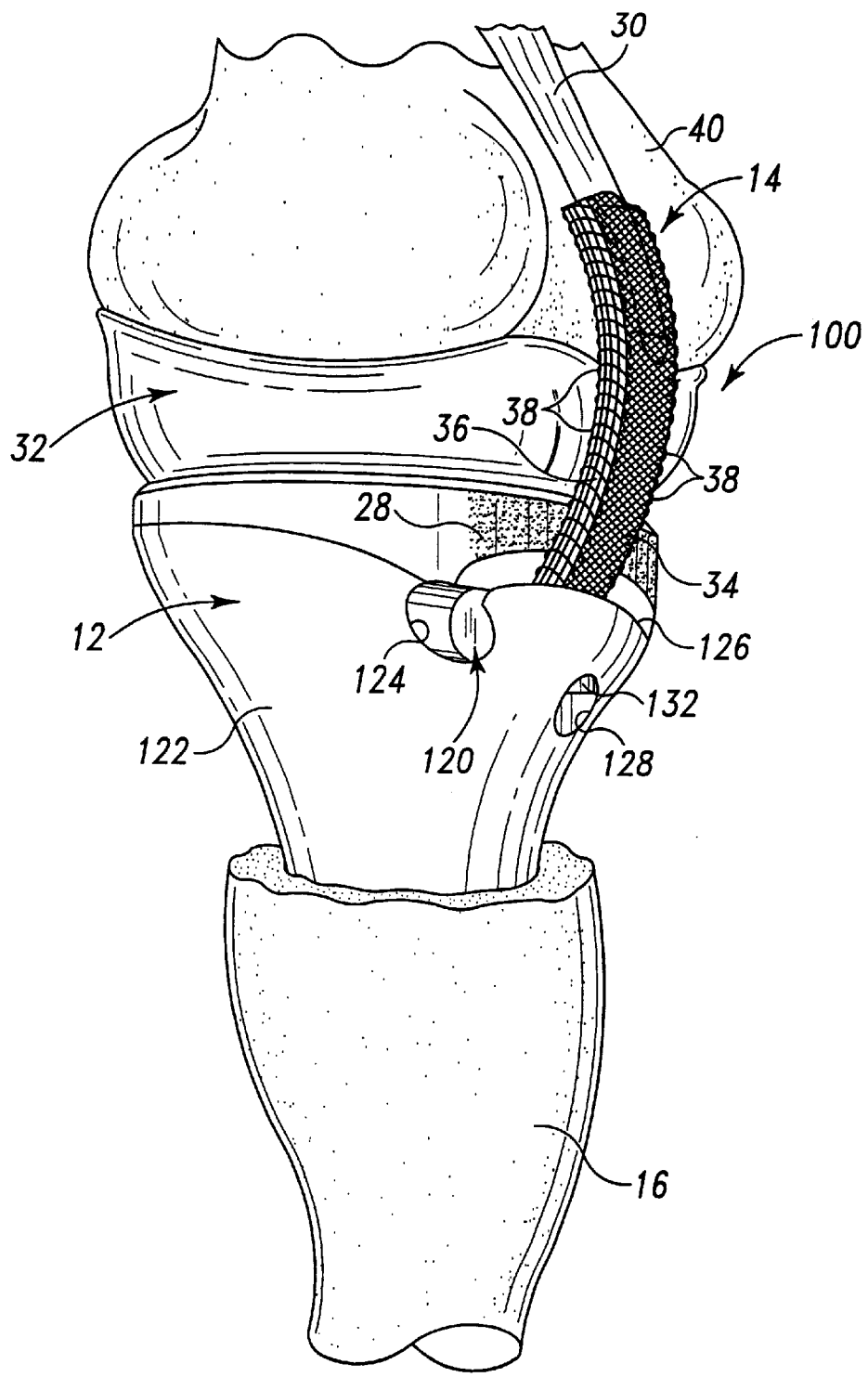
FIG. 4 is a fragmentary perspective view which shows the prosthesis assembly of FIG. 3 secured to a patient's femur.

Referring now to FIGS. 3 and 4, there is shown another embodiment of a prosthesis assembly (hereinafter referred to with reference numeral 100) which incorporates the features of the present invention therein. The prosthesis assembly 100 is somewhat similar to the prosthesis assembly 10. Accordingly, the prosthesis assembly 100 includes a number of features and components which are identical to certain of the features and components previously discussed in regard to the prosthesis assembly 10. The same reference numerals are utilized in FIGS. 3 and 4 to designate identical features which were previously discussed in regard to FIGS. 1 and 2 and additional discussion thereof is not warranted.

The prosthesis assembly 100 includes a tibial prosthesis 112 which has a body 122. The body 122 of the tibial prosthesis 112 is essentially the same as the body 22 of the tibial prosthesis 12 except that the body 122 has a number of features defined therein which facilitate securement of the band assembly 14 to the body 122 by use of a different retaining member 18. Specifically, the retaining bar 20 of the prosthesis assembly 10 has been replaced in the prosthesis assembly 100 with a different type of retaining member such as a retaining pin 120.

Similarly to the retaining bar 20, the retaining pin 120 is provided to secure the band assembly 14 to the tibial prosthesis 112. In particular, the bands 34, 36 are positionable around a portion of the outer periphery of the retaining pin 120 (i.e. a retaining portion of the pin 120) in order to secure the band assembly 14 to the body 122 of the tibial prosthesis 112. Indeed, the body 122 of the tibial prosthesis 112 has a pin receiving slot 124 and a band receiving slot 126 defined therein. Once the bands 34, 36 of the band assembly 14 have been positioned around the retaining pin 120, the retaining pin 120 is then slid or otherwise advanced into the pin receiving slot 124 such that the end portions of the bands 34, 36 extend outwardly through the band receiving slot 126.

A threaded fastener opening 128 is defined in the body 122 of the tibial prosthesis 112 and extends from the outside surface of the body 122, through the body 122, and into the pin receiving slot 124. In such a manner, a fastener such as a bolt or screw 132 may be advanced through the fastener opening 128 and into contact with the retaining pin 120 and/or the band assembly 14 thereby securing the retaining pin 120 (and hence the band assembly 14) within the pin receiving slot 124.

Once the retaining pin 120 has been secured to the tibial prosthesis 12 in such a manner, the patellar ligament 30 may then be secured to the band assembly 14 in the manner previously described in regard to the prosthesis assembly 10. In particular, the patellar ligament 30 may be interposed between, and thereafter sutured to, the end portions of the bands 34, 36 extending out of the band receiving opening 126 in the same manner as described above so as to mechanically secure the patellar ligament 30 to the tibial prosthesis 112.

As shown in FIG. 3, a portion 130 of the body 122, along with the retaining pin 120, may have the porous material 28 disposed thereon. As described above, such use of the porous material 28 enhances tissue ingrowth which facilitates long-term attachment of the patellar ligament 30 to the body 122 and the pin 120 and hence the tibial prosthesis 112.

The aforedescribed prosthesis assemblies 10, 100 have a number of advantages over heretofore designed prosthesis assemblies. For example, the configuration of the band assembly 14 not only provides the mechanical strength necessary to secure the patellar ligament 30 to the tibial prosthesis 12, 112, but also facilitates tissue ingrowth. Specifically, the presence of the resorbable inner band 36 promotes growth of the patellar ligament 30 in the direction toward the tibial prosthesis 12, 112. In such a manner, ingrowth of the patellar ligament 30 into the porous coating 28 disposed on the body 22, 122 and retaining members 18 of the tibial prosthesis 12, 112 is facilitated. It should be appreciated that attachment of the patellar tendon 30 by ingrowth to the tibial prosthesis 12, 112 provides the desirable, long-term form of attachment that closely reproduces natural attachment of the patellar ligament 30 to a natural tibia. Hence, attachment of the patellar ligament 30 by use of the band assembly 14 not only provides the short-term mechanical attachment requirements of the joint replacement procedure, but also facilitates long-term, permanent attachment of the patellar ligament 30 to the tibial prosthesis 12, 112.

Operation of the Present Invention

In operation, the prosthesis assemblies 10, 100 of the present invention are utilized in the performance of a knee replacement procedure in order to attach the distal end portion of the patellar ligament 30 to the artificial tibial prosthesis 12, 112 which has been implanted into the patient's tibia 16. In particular regard to the prosthesis assembly 10, the tibial prosthesis 12 is first implanted into the medullary canal of the patient's tibia 16 such that the body 22 of the tibial prosthesis 12 extends out of the patient's tibia 16 in the manner shown in FIG. 2.

Once implanted in such a manner, the bearing insert 32 is secured to the proximal end of the tibial prosthesis 12. Thereafter, the distal end of the patient's femur 40 is positioned relative the tibial prosthesis 12 such that the lateral and medial condyles of the distal end of the patient's femur 40 contact the bearing insert 32. Such contact with the bearing insert 32 provides a suitable artificial surface on which the distal end of the patient's femur 40 may bear.

Thereafter, the band assembly 14 is looped around the retaining bar 20 and thereafter secured to the patellar ligament 30. In particular, one end of the bands 34, 36 is advanced around the retaining bar 20 such that both ends of the bands 34, 36 extend outwardly from the retaining bar 20. The distal end of the patellar ligament 30 is then sandwiched or otherwise interposed between the respective end portions of the bands 34, 36. In such a configuration the patellar ligament 30 is interposed between the end portions of the inner band 36 which are, in turn, interposed between the end portions of the outer band 34. Thereafter, the patellar ligament 30 is sutured to the bands 34, 36 by use of a number of sutures 38 thereby securing the patellar ligament 30 to the band assembly 14 and hence the tibial prosthesis 12.

It should be appreciated that the order of certain of the steps of the above described procedure may be altered. For example, the bands 34, 36 of the band assembly 14 may be looped around the retaining bar 20 prior to implantation of the tibial prosthesis 12 into the tibia 16. In the alternative, even if not looped around the retaining bar 20 prior to implantation of the tibial component 12, the band assembly 14 may be looped around the retaining bar 20 prior to alignment of the patient's femur 40 with the bearing insert 32. In short, the band assembly 14 may be looped around the retaining bar 20 at any time in the procedure prior to suturing of the patellar ligament 30 thereto.

In particular regard to the prosthesis assembly 100, the tibial prosthesis 112 is first implanted into the medullary canal of the patient's tibia 16 such that the body 122 of the tibial prosthesis 112 extends out of the patient's tibia 16 in the manner shown in FIG. 4. Thereafter, the bearing insert 32 is secured to the proximal end of the tibial prosthesis 112. The distal end of the patients femur 40 is then positioned relative the tibial prosthesis 112 in a manner similar to as discussed above.

Thereafter, the bands 34, 36 are advanced around a portion of the outer periphery of the retaining pin 120 (i.e. the retaining portion of the pin 120). The retaining pin 120 is then secured to the body 122 of the tibial prosthesis 112 by sliding or otherwise advancing into the retaining pin 120 into the pin receiving slot 124 such that the end portions of the bands 34, 36 extend outwardly through the band receiving slot 126. The screw 132 is the advanced through the fastener opening 128 and into contact with the retaining pin 120 and/or the band assembly 14 thereby securing the retaining pin 120 (and hence the band assembly 14) within the pin receiving slot 124.

Once the retaining pin 120 has been secured to the tibial prosthesis 112 in such a manner, the patellar ligament 30 may then be secured to the band assembly 14 in the manner previously described in regard to the prosthesis assembly 10. In particular, the patellar ligament 30 is interposed between and thereafter sutured to the end portions of the bands 34, 36 extending out of the band receiving opening 126 in the same manner as described above thereby mechanically securing the patellar ligament 30 to the band assembly 14 and hence the tibial prosthesis 112.

Similarly to as described above in regard to the prosthesis assembly 10, it should be appreciated that the order of certain of the steps of the above described procedure may be altered. For example, the retaining pin 120 (with bands 34, 36 of the band assembly 14 looped therearound) may be advanced into the pin receiving slot 124 prior to implantation of the tibial prosthesis 12 into the tibia 16. In the alternative, even if not positioned in the pin receiving slot 124 prior to implantation of the tibial component 12, the retaining pin 120 (with bands 34, 36 of the band assembly 14 looped therearound) may be advanced into the pin receiving slot 124 prior to alignment of the patient's femur 40 with the bearing insert 32. In short, the retaining pin 120 (with bands 34, 36 of the band assembly 14 looped therearound) may be advanced into the pin receiving slot at any time in the procedure (including after suturing of the patellar ligament 30 to the band assembly 14).

Hence, as described herein, the prosthesis assemblies 10, 100 of the present invention provide numerous advantages over heretofore designed prosthesis assemblies. For example, the band assembly 14 provides a relatively large suture surface compared to heretofore designed systems thereby providing initial mechanical securement advantages. Moreover, as described above, the configuration of the band assembly 14 not only provides the mechanical strength necessary to secure the patellar ligament 30 to the tibial prosthesis 12, 112, but it also facilitates tissue ingrowth. In particular, during the time period initially following the joint replacement procedure, the outer band 34 provides the mechanical strength (e.g. the tensile strength) to maintain attachment of the patellar ligament 30 to the tibial prosthesis 12, whereas the resorbable material (e.g. SIS) associated with the inner band 36 stimulates or otherwise facilitates growth of the patellar ligament 30 in a direction toward the tibial prosthesis 12. Over time, the resorbable material of the inner band 36 is absorbed by the patient's body during continued growth of the patellar ligament 30. During such absorption of the inner band 36, the outer band 34 continues to provide the mechanical strength necessary to keep the growing patellar ligament 30 attached to the tibial prosthesis 12 thereby making up for any mechanical loss caused by the dissolving outer band 34. Eventually, the patellar ligament 30 grows to a point in which it begins to ingrow into the porous material 28 associated with the retaining members 18 and the body 22, 122 of the tibial prosthesis 12, 112. As described above, such ingrowth of the patellar ligament 30 into the porous material 28 enables long-term attachment of the patellar ligament 30 to the tibial prosthesis 12, 112.

While the invention has been illustrated and described in detail in the drawings and foregoing description, such an illustration and description is to be considered as exemplary and not restrictive in character, it being understood that only the preferred embodiments have been shown and described and that all changes and modifications that come within the spirit of the invention are desired to be protected.

There are a plurality of advantages of the present invention arising from the various features of the prosthesis assembly and associated method described herein. It will be noted that alternative embodiments of the prosthesis assembly and associated method of the present invention may not include all of the features described yet still benefit from at least some of the advantages of such features. Those of ordinary skill in the art may readily devise their own implementations of a prosthesis assembly and associated method that incorporate one or more of the features of the present invention and fall within the spirit and scope of the present invention as defined by the appended claims.

For example, it should be appreciated that although the prosthesis assemblies 10, 100 are herein described as being utilized in conjunction with a natural human femur 40, the prosthesis assemblies 10, 100 of the present invention may also be utilized in conjunction with an implanted femoral component.

What is claimed is:

1. A prosthesis assembly, comprising:
    a prosthesis including a retaining member;
    a first band constructed of a resorbable material, said first band having a first end portion, a middle portion, and a second end portion; and
    a second band constructed of a biologically inert material, said second band having a first end portion, a middle portion, and a second end portion,
    wherein (i) said middle portion of said first band is positioned around a retaining portion of said retaining member such that both said first end portion and said second end portion of said first band extend outwardly from said retaining member, (ii) said middle portion of said second band is positioned around said retaining portion of said retaining member such that both said first end portion and said second end portion of said second band extend outwardly from said retaining member, and (iii) each of said first end portion of said first band, said second end portion of said first band, said first end portion of said second band, and said second end portion of said second band is adapted to be secured to a soft tissue member,
    wherein each of (i) said soft tissue member, (ii) said first end portion of said first band, and (iii) said second end portion of said first band is interposed between said first end portion of said second band and said second end portion of said second band when said first band and said second band are secured to said soft tissue member.

2. A prosthesis assembly, comprising:
    a prosthesis including a retaining member;
    a first band constructed of a resorbable material, said first band having a first end portion, a middle portion, and a second end portion; and
    a second band constructed of a biologically inert material, said second band having a first end portion, a middle portion, and a second end portion,
    wherein (i) said middle portion of said first band is positioned around a retaining portion of said retaining member such that both said first end portion and said second end portion of said first band extend outwardly from said retaining member, (ii) said middle portion of said second band is positioned around said retaining portion of said retaining member such that both said first end portion and said second end portion of said second band extend outwardly from said retaining member, and (iii) each of said first end portion of said first band, said second end portion of said first band, said first end portion of said second band, and said second end portion of said second band is adapted to be secured to a soft tissue member,
    wherein each of (i) said soft tissue member, (ii) said first end portion of said second band, and (iii) said second end portion of said second band is interposed between said first end portion of said first band and said second end portion of said first band when said first band and said second band are secured to said soft tissue member.

3. The apparatus of claim 1, wherein said resorbable material includes a xenograft material.

4. The apparatus of claim 1, wherein said resorbable material is selected from a group consisting of SIS, PDS, PGA, and PLLA.

5. The apparatus of claim 1, wherein said biologically inert material includes a cobalt-chrome material.

6. The apparatus of claim 1, wherein said prosthesis is constructed of metal.

7. The apparatus of claim 1, wherein:

said retaining member includes a pin, said prosthesis has a pin receiving slot and a band receiving slot defined therein, said pin is positionable in said pin receiving slot of said prosthesis, and each of said first end portion of said first band, said second end portion of said first band, said first end portion of said second band, and said second end portion of said second band extends outwardly from said band receiving slot when said pin is positioned in said pin receiving slot.

8. The apparatus of claim 1, wherein:

said retaining member includes a retaining bar, said prosthesis has a channel defined therein, said retaining bar extends across said channel of said prosthesis, said middle portion of said first band is positioned in said channel of said prosthesis such that both said first end portion and said second end portion of said first band extend outwardly from said channel, and said middle portion of said second band is positioned in said channel of said prosthesis such that both said first end portion and said second end portion of said second band extend outwardly from said channel.

9. A prosthesis assembly, comprising:

a prosthesis including a retaining member;

a first band constructed of a resorbable material, said first band having a first end portion, a middle portion, and a second end portion; and a second band constructed of a biologically inert material, said second band having a first end-portion, a middle portion, and a second end portion, wherein (i) said middle portion of said first band is positioned around a retaining portion of said retaining member such that both said first end portion and said second.end portion of said first band extend outwardly from said retaining member, (ii) said middle portion of said second band is positioned around said retaining portion of said retaining member such that both said first end portion and said second end portion of said second band extend outwardly from said retaining member, and (iii) each of said first end portion of said first band, said second end portion of said first band, said first end portion of said second band, and said second end portion of said second band is secured to a soft tissue member, wherein said retaining member includes a retaining bar, wherein said prosthesis has a channel defined therein, wherein said retaining bar extends across said channel of said prosthesis, wherein said middle portion of said first band is positioned in said channel of said prosthesis such that both said first end portion and said second end portion of said first band extend outwardly from said channel, and said middle portion of said second band is positioned in said channel of said prosthesis such that both said first end portion and said second end portion of said second band extend outwardly from said channel, wherein said prosthesis includes a number of sidewalls which collectively define said channel, and wherein both said retaining bar and said number of sidewalls have a porous coating disposed thereon.

10. A prosthesis assembly, comprising:

a prosthesis having a retaining member, said retaining member having a retaining surface;

an inner band having a first end portion, a middle portion, and a second end portion; and an outer band having a first end portion, a middle portion, and a second end portion, wherein (i) said middle portion of said inner band is positioned in contact with said retaining surface of said retaining member such that both said first end portion and said second end portion of said inner band extend outwardly from said retaining member, (ii) said outer band is secured to said inner band such that (a) said first end portion of said outer band is positioned in contact with said first end portion of said inner band, (b) said middle portion of said outer band is positioned in contact with said middle portion of said inner band, and (c) said second end portion of said outer band is positioned in contact with said second end portion of said inner band, and (iii) each of said first end portion of said inner band, said second end portion of said inner band, said first end portion of said outer band, and said second end portion of said outer band is adapted to be secured to a soft tissue member, wherein said soft tissue member is interposed between (i) said first end portion and said second end portion of said inner band, and (ii) said first end portion and said second end portion of said outer band when said first band and said second band are secured to said soft tissue member.

11. The apparatus of claim 10, wherein:

said inner band is constructed of a resorbable material, and said outer band is constructed of a biologically inert material.

12. The apparatus of claim 10, wherein:

said inner band is constructed of a biologically inert material, and said outer band is constructed of a resorbable material.

13. The apparatus of claim 10, wherein said prosthesis is constructed of metal.

14. A prosthesis assembly, comprising:

a prosthetic component having a retaining member;

a first band constructed of a resorbable material, said first band being adapted to be secured to both said retaining member and said soft tissue member; and a second band constructed of a biologically inert material, said second band being adapted to be secured to both said retaining member and said soft tissue member, wherein said soft tissue member is interposed between (i) a first end and a second end of said first band, and (ii) a first end and a second end of said second band when said first band and said second band are secured to said soft tissue member.

15. The prosthesis assembly of claim 14, wherein said resorbable material includes a xenograft material.

16. The prosthesis assembly of claim 14, wherein said resorbable material is selected from a group consisting of SIS, PDS, PGA, and PLLA.

17. The prosthesis assembly of claim 14, wherein said biologically inert material includes a cobalt-chrome material.

18. The prosthesis assembly of claim 14, wherein said prosthesis is constructed of metal.

19. The apparatus of claim 2, wherein said resorbable material includes a xenograft material.

20. The apparatus of claim 2, wherein said resorbable material is selected from a group consisting of SIS, PDS, PGA, and PLLA.

21. The apparatus of claim 2, wherein said biologically inert material includes a cobalt-chrome material.

22. The apparatus of claim 2, wherein said prosthesis is constructed of metal.

23. The apparatus of claim 2, wherein:

said retaining member includes a pin, said prosthesis has a pin receiving slot and a band receiving slot defined therein, said pin is positionable in said pin receiving slot of said prosthesis, and each of said first end portion of said first band, said second end portion of said first band, said first end portion of said second band, and said second end portion of said second band extends outwardly from said band receiving slot when said pin is positioned in said pin receiving slot.

24. The apparatus of claim 2, wherein:

said retaining member includes a retaining bar, said prosthesis has a channel defined therein, said retaining bar extends across said channel of said prosthesis, said middle portion of said first band is positioned in said channel of said prosthesis such that both said first end portion and said second end portion of said first band extend outwardly from said channel, and said middle portion of said second band is positioned in said channel of said prosthesis such that both said first end portion and said second end portion of said second band extend outwardly from said channel.

* * * * *